United States Patent
Grueneberg

(10) Patent No.: US 7,636,156 B2
(45) Date of Patent: Dec. 22, 2009

(54) WAFER INSPECTION SYSTEM AND METHOD

(75) Inventor: Dirk Grueneberg, Dresden (DE)

(73) Assignee: Qimonda AG, Munich (DE)

( * ) Notice: Subject to any disclaimer, the term of this patent is extended or adjusted under 35 U.S.C. 154(b) by 356 days.

(21) Appl. No.: 11/763,837

(22) Filed: Jun. 15, 2007

(65) Prior Publication Data

US 2008/0309927 A1 Dec. 18, 2008

(51) Int. Cl.
  *G01N 21/00* (2006.01)
(52) U.S. Cl. .................................. 356/237.5
(58) Field of Classification Search ............ 356/237.5; 324/750
  See application file for complete search history.

(56) References Cited

U.S. PATENT DOCUMENTS

| | | | |
|---|---|---|---|
| 6,252,412 B1 * | 6/2001 | Talbot et al. ................ | 324/750 |
| 7,013,222 B2 * | 3/2006 | Strader ........................ | 702/30 |
| 2004/0028267 A1 | 2/2004 | Shoham et al. | |
| 2005/0023491 A1 | 2/2005 | Young et al. | |
| 2005/0036671 A1 | 2/2005 | Watkins et al. | |
| 2005/0038554 A1 | 2/2005 | Watkins | |
| 2005/0060104 A1 | 3/2005 | Strader | |
| 2005/0146714 A1 | 7/2005 | Kitamura et al. | |
| 2005/0213085 A1 | 9/2005 | Lee et al. | |

FOREIGN PATENT DOCUMENTS

EP 1296351 3/2003

* cited by examiner

*Primary Examiner*—Roy Punnoose
(74) *Attorney, Agent, or Firm*—Dicke, Billig & Czaja, PLLC

(57) ABSTRACT

A wafer inspection system and method is disclosed. On embodiment includes an edge defect detection unit, an optical inspection unit and a processor unit. The edge defect detection unit is configured to detect defects occurring in an edge area of the wafer and to record edge defect positions. The optical inspection unit is configured to capture images of functional devices in a functional area of the wafer surrounded by the edge area and to record device defect positions related to the functional devices. The processor unit is configured to output a data set relating the edge and device defect positions to the same coordinate system.

22 Claims, 3 Drawing Sheets

- Detect defects in edge area — 302
- Record edge defect positions — 304
- Capture images of functional devices — 306
- Record device defect positions — 308
- Compile data set of edge and device defect positions referred to the same coordinate system — 310

410

WAFER INSPECTION SYSTEM AND METHOD

BACKGROUND

During fabrication of integrated circuits such as, for example, volatile or non-volatile memory devices, analog circuits or logic circuits, various semiconductor fabrication processes are applied to a semiconductor wafer. After a predetermined sequence of fabrication processes, analyzing steps are carried out to check the proper performance of the fabrication processes.

For example, after patterning processes, e.g., after development of an exposed resist layer or after a masked etch process, optical inspection methods may be performed. A high resolution camera captures images of or a laser scans sections of the wafer that may be assigned to functional devices, e.g., integrated circuits. The captured images are compared against each other or a reference image to identify deviations in the patterns that may be interpreted as defects. The identified defects are assigned to a device coordinate system identifying the corresponding device on the wafer and the position of the defect with reference to a local coordinate system referencing to the respective functional device.

The use of optical inspection tools, which are based on the comparison of images or patterns is restricted to a functional, printed area of the wafer that is accessible for lithographic tools. A narrow edge area of the wafer that extends along the outer edge of the wafer and that surrounds the functional area is typically not accessible for lithographic tools. As no or only fragmentary patterns are printed in the edge area, defects occurring there are not detectable by an optical inspection tool which is based on an image comparison of patterned sections.

A typical wafer edge defect inspection tool includes an inspection system with one or more inspection cameras or laser scanners that scan the edge area for defects on both surfaces of the wafer. For this purpose, either the wafer is fixed and the inspection system is directed along the perimeter of the wafer or the inspection system is fixed and the wafer is rotated to scroll the perimeter versus the inspection system. Typically, the position of defects detected by the edge defect inspection tool is referenced to a mark, which may be a notch or a flattened section in the perimeter of the wafer in terms, for example, of a polar coordinate system or a distance between the defect and the mark on the perimeter.

A need exists for a wafer inspection system that makes feasible a thorough defect analysis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Figure 1:
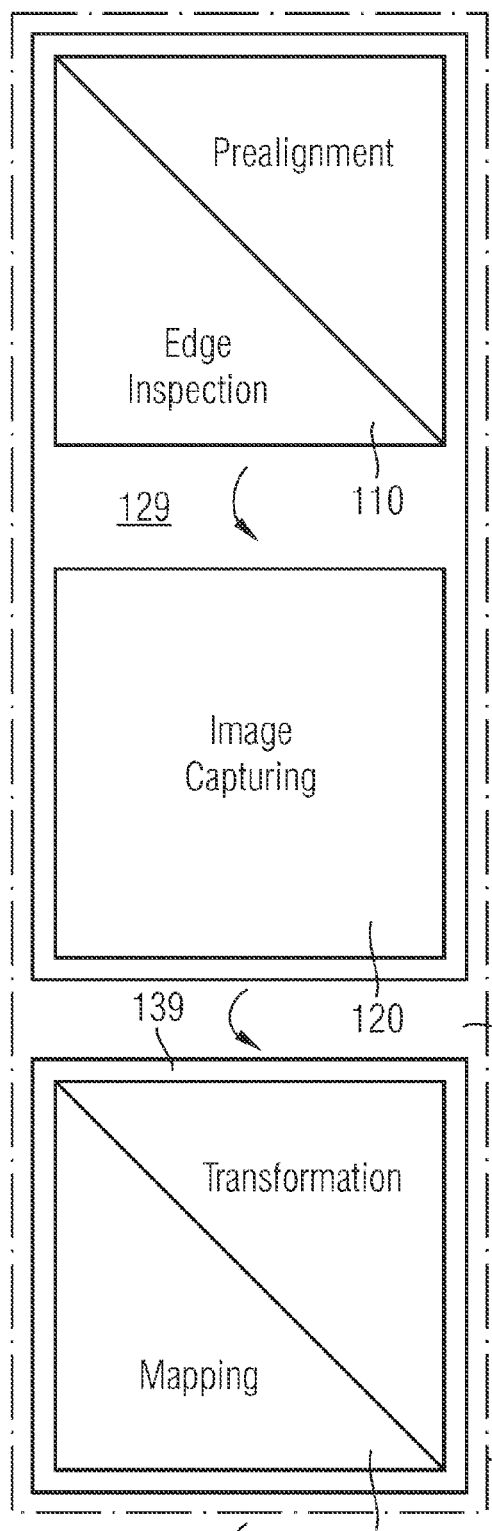
FIG. 1 is a simplified schematic illustration of a wafer inspection system according to an embodiment.
Figure 1:
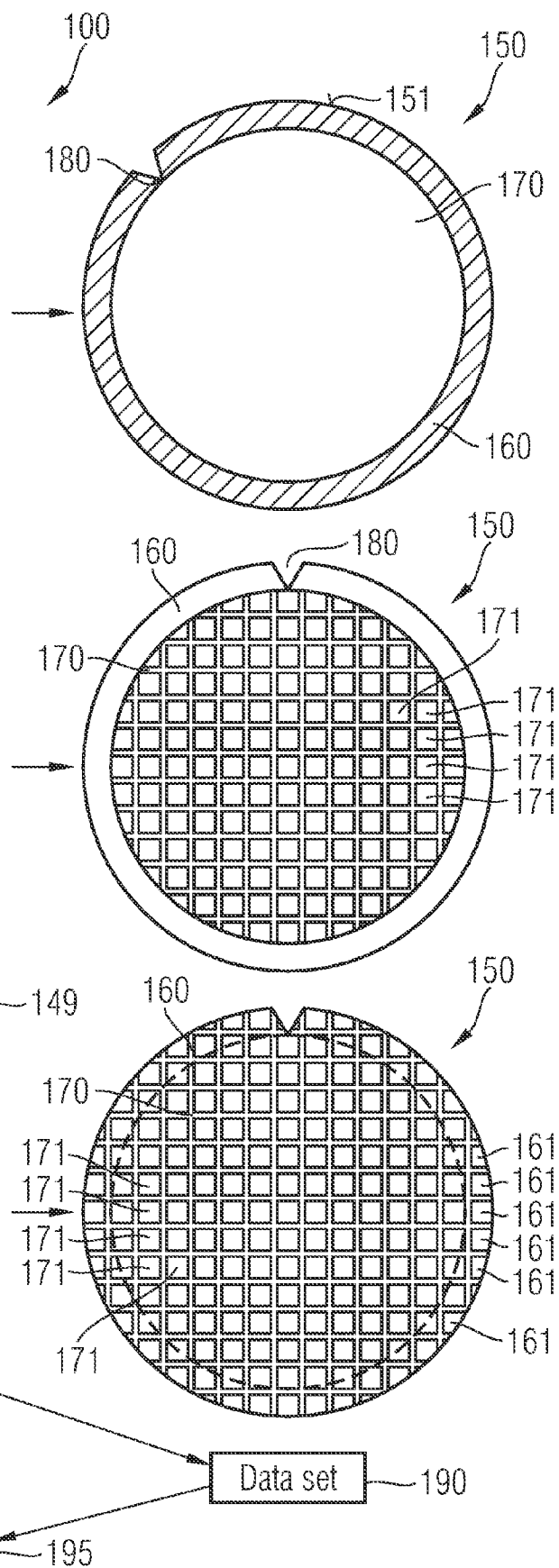

FIG. 1 illustrates on the left-hand side a wafer inspection system 100 including an edge defect detection unit 110, an optical inspection unit 120 and a processor unit 130. On the right-hand side of FIG. 1, a wafer 150 is illustrated, wherein for each unit 110, 120, 130 of the wafer inspection system 100 those regions of the wafer 150 are highlighted that are evaluated by the respective unit 110, 120, 130.

The wafer 150 includes a functional area 170 and an edge area 160 that surrounds the functional area 170 and that extends along a wafer edge 151 of the wafer 150. The width of the edge area 160 is a few millimeters, for example, three millimeters. A mark 180 at the wafer edge 151 supports the alignment of the wafer 150 to inspection and fabrication tools. According to this exemplary embodiment, the mark 180 is a notch. According to other embodiments, the mark may be a flattened section of the edge 151. In the edge region 160, various processes, for example deposition processes may not sufficiently conform for the proper application of further processes, for example, of patterning processes as, for example, along the wafer edge 151, a plasma is not sufficiently homogeneous during a plasma supported deposition process. As a consequence, deposited layers taper off versus the wafer edge 151 leaving the edge area 160 not suitable for subsequent patterning processes. Lithographic patterning processes are typically avoided in the edge area 160.

When the wafer 150 is supplied to the wafer inspection system 100, it may be at first subjected to an edge defect scan at the edge defect detection unit 110 which is configured to detect defects occurring in the edge area 160 of the wafer 150 and which is further configured to record edge defect positions related to the identified defects in the edge area 160. The edge defect detection unit may include optical cameras and/or laser scanners.

The edge defect inspection may be combined with a pre-alignment of the wafer 150, in course of which the wafer 150 is rotated until the mark 180 arrives at a predetermined position.

During the edge defect inspection, the hatched edge area 160 of the wafer 150 as illustrated on the right-hand side of FIG. 1 may be inspected.

Then the wafer 150 may be fed to the optical inspection unit 120 of the wafer inspection system 100. The optical inspection unit 120 is configured to capture images of functional devices 121 in a functional area 170 of the wafer 150 and is further configured to record device defect positions related to the functional devices 171. The optical inspection unit 110 may be configured to scan the functional devices 171 for defects through an image comparison, wherein the captured images are either compared against each other or against reference images. As deposition and etch processes in the edge area are typically not sufficiently conformal, the edge area 160 is masked out for the purpose of the optical inspection performed through the optical inspection unit 120. Typically, an image comparison in the edge area 160 would lead to the detection of a multitude of defects, wherein the majority of defects result from known, typical edge phenomena, for example tapering layers, and conceals specific defects resulting from an untypical abnormality of the evaluated process.

According to one or more embodiments, the order of edge defect inspection and optical inspection of the functional area may be inverted. In an exemplary embodiment, the edge inspection is performed during an alignment of the wafer 150 to the optical inspection unit 120. The defects identified through the optical inspection unit 120 may be referenced to a device coordinate system that identifies a respective functional device and a local position related to the respective functional device. The defects identified during the edge defect inspection, however, are typically referenced to the perimeter of the wafer 150, for example in terms of a distance to the center of the wafer and an angle towards the mark 180 or in terms of a distance on the perimeter between the defect position and the mark 180. The defects detected through the optical inspection unit 120 and the edge defect detection unit 110 are of different types. Though the defects identified in the edge area 160 may also be identified by optical image comparison, the images that are compared are other ones than the images that are necessary to detect defects in the functional area 170.

The processor unit 130 is configured to output a data set 190 that relates both edge and device defect positions to the same coordinate system, which may be a polar coordinate system, a device orientated coordinate system or a Cartesian coordinate system.

According to one embodiment, the edge defect positions are transformed into a device orientated coordinate system, to which the optical inspecting unit 120 refers the detected defects typically, in order to reduce calculating complexity. Further, the processor unit 130 may be capable of mapping the transformed edge defect positions to virtual devices 161 assigned to the edge area 160. As illustrated on the right-hand side of the processor unit 130, the data set may be amended with virtual devices 161 that are aligned to a grid to which the functional devices 171 are aligned in the functional area 170 and that is extended into the edge area 160. Defects in the edge area 160 on the wafer backside and/or at the edge may be neglected, mapped to the corresponding virtual device 161 on the wafer front side or to further virtual devices.

The data set 190 may be analyzed automatically in a combined defect analysis unit 195 or by the operator. The combined data set 190 includes defect data related to both the edge area 160 and the functional area 170 and may be, for example, subjected to statistical routines similar to those that are applied to that of the functional devices 171. Though the defect information regarding the edge area 160 and the functional area 170 are integrated in the same data set 190, the defect information concerning the edge defects differs from that of device defects. A device defect indicates that a pattern within a functional device deviates from the expected pattern more than admissible. The concerned device is defined as being faulty. The defect information concerning the virtual devices 161 contains the information that in the respective sub-area the edge section does not look like it should. A virtual device 161 with no edge defects assigned to it does not represent a defect-free functional device but an inconspicuous sub-region of the edge area 160.

The joint analysis of edge defects and defects in the functional area may deliver a profound insight of process abnormalities. For example, defects assigned to a partial tail in the functional area may be assigned to a breakout of material at the edge of a deposited layer. Due to an inhomogeneous plasma near the notch, the latter may be the source of particles broken away from the deposited layer. These particles spread over the wafer forming a tail pointing to the notch. This effect may be amplified by drawing the wafer out of a process liquid with the notch ahead. Inspecting the combined database may facilitate learning about interrelationships between process deviations concerning the edge region and device defects.

The wafer inspection system 100 may further include a rotative support unit that is configured to align the wafer to the optical inspection device 120. In this case, the edge defect detection unit 110 may be further configured to inspect the edge area 160 during the alignment.

According to another embodiment, the edge defect detection unit 110 is further configured to inspect the edge area 160 of a successor wafer during the optical inspection of an antecessor wafer at the optical inspection unit 120. With regard to a wafer lot, the required time to perform the edge inspection and the optical inspection of the functional area may be reduced.

Figure 2:
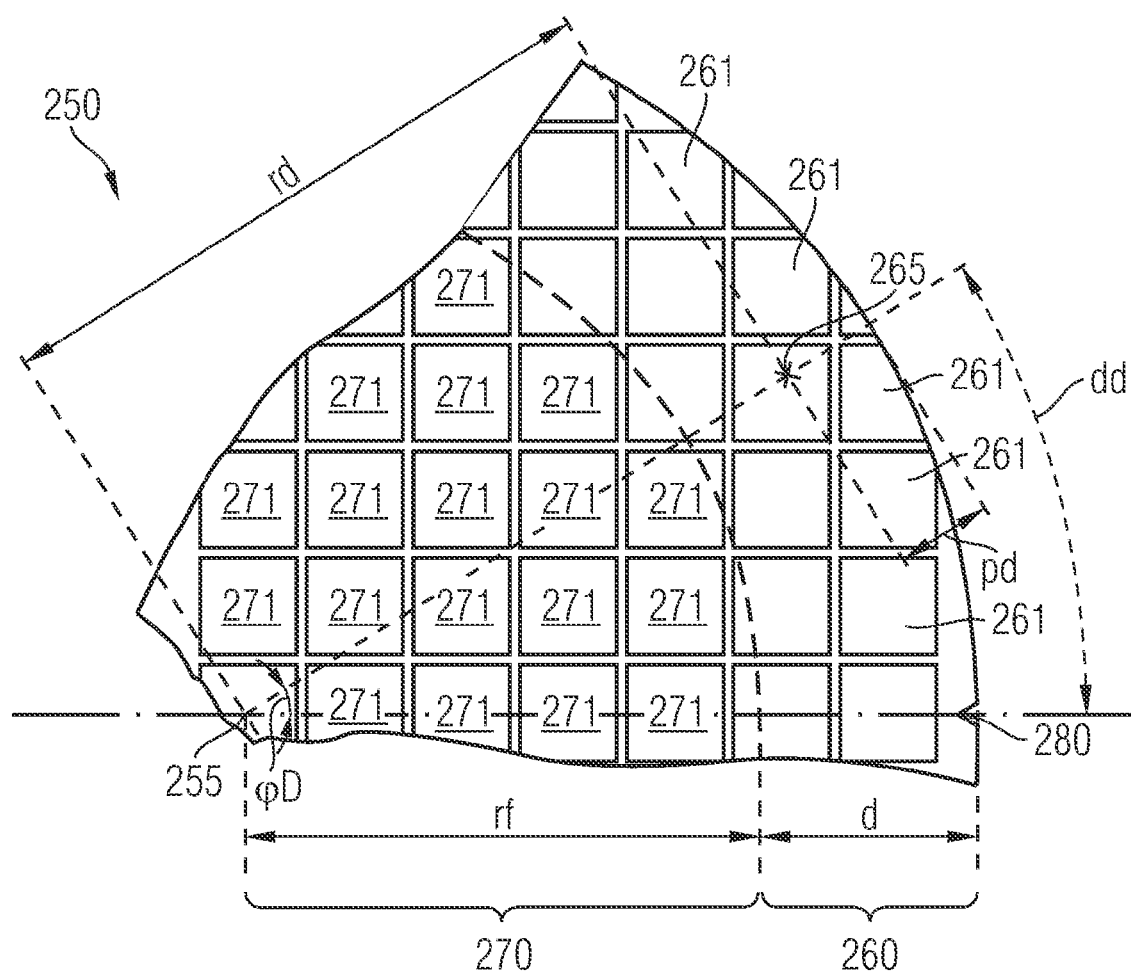
FIG. 2 is a simplified illustration of a section of a wafer for illustrating the mapping of edge defects to virtual functional devices according to another embodiment.

FIG. 2 illustrates a section of a pattern surface of a wafer 250. The wafer 250 includes a functional area 270 that corresponds essentially to a circular area with a radius rf in the center of the wafer 250. An annular edge region 260 surrounds the functional area 270. The width d of the annulus is, for example, less than five millimeters, for example three millimeters. Defects in the functional area 270 are detected by an optical inspection unit of the wafer inspection system as described with reference to FIG. 1, and may be assigned to functional devices 271. The functional devices 271 may represent a prestage of an integrated circuit, for example a memory chip or a section thereof. According to an exemplary embodiment, defects in the functional area 270 are related to a device coordinate system that identifies the respective functional device 271 and the position of the defect with reference to the respective functional device 271, for example to a corner point of the respective functional device 271. The functional devices 271 are arranged in rows and columns forming a grid. In one embodiment, narrow kerfs separate the functional devices 271 from each other.

Edge defects occurring in the edge area 260 may be identified, for example, through an inspection tool, for example an optical camera or a laser scanner, wherein either the wafer 250 is fixed and the inspection tool is directed along the perimeter of the wafer or the inspection tool is fixed and the wafer is rotated such that the inspection tool may inspect the edge area 260.

The edge defect position of a defect 265 may be recorded with reference to a lithographic alignment mark on the top surface of the wafer 250 or, as illustrated in the example of FIG. 2, with reference to a notch 280 at the wafer edge and the center of a wafer 250. The position may be defined by a distance dd between the defect 265 and the notch 280 on the perimeter of the wafer 250 and the distance pd between the defect 265 and the edge or with reference to a distance rd between the defect 265 and a wafer midpoint 255 and an angle φd between the radius of the defect 265 and the notch 280. According to another embodiment, the edge defect positions may be recorded with respect to a lithographic alignment mark on the top surface of the wafer 250 in terms of a Cartesian coordinate system.

The edge defect positions sampled by the edge inspection tool are transformed into the coordinate system to which the defect positions in the functional area 270 are referenced. According to this example, the coordinate system is a device oriented coordinate system, wherein sub-regions of the edge area 260 are assigned to virtual devices 261. The identified edge defect positions are then assigned to the respective virtual devices 261. Defects in the edge area 260 on the wafer backside and/or at the edge may be neglected, mapped to the corresponding virtual device 261 on the wafer front side or to further virtual devices.

The compiled data set assigns to each detected defect an information identifying the concerned chip or device, the coordinates of the detected defect related to the device, for example to a corner of the device, the defect size, further parameters of the defect and an information identifying the concerned device as one of the functional devices or one of the virtual devices. In a sequence of manufacturing processes, the wafer may be inspected after each process of interest to obtain an updated data set.

An integration of an edge defect detection unit and an optical inspection unit in the same wafer inspection system facilitates the alignment of the data sets of the recorded edge defect positions and the recorded device defect positions, as the wafer is aligned only one time and both inspections refer to the same wafer position. If the wafer is first aligned to an edge defect detection unit, for example, a stand-alone edge defect detection system and then transferred to another system, which includes the optical inspection unit, the wafer must be realigned and precautionary measures must be taken to adjust correctly the two data sets against each other.

Further, as the edge defect inspection may be carried out during the alignment of the wafer to the optical inspection device, the edge area of a successor wafer of a wafer lot may be inspected during the optical inspection of an antecessor wafer of the same lot such that the overall inspection time may be reduced significantly.

Figure 3:
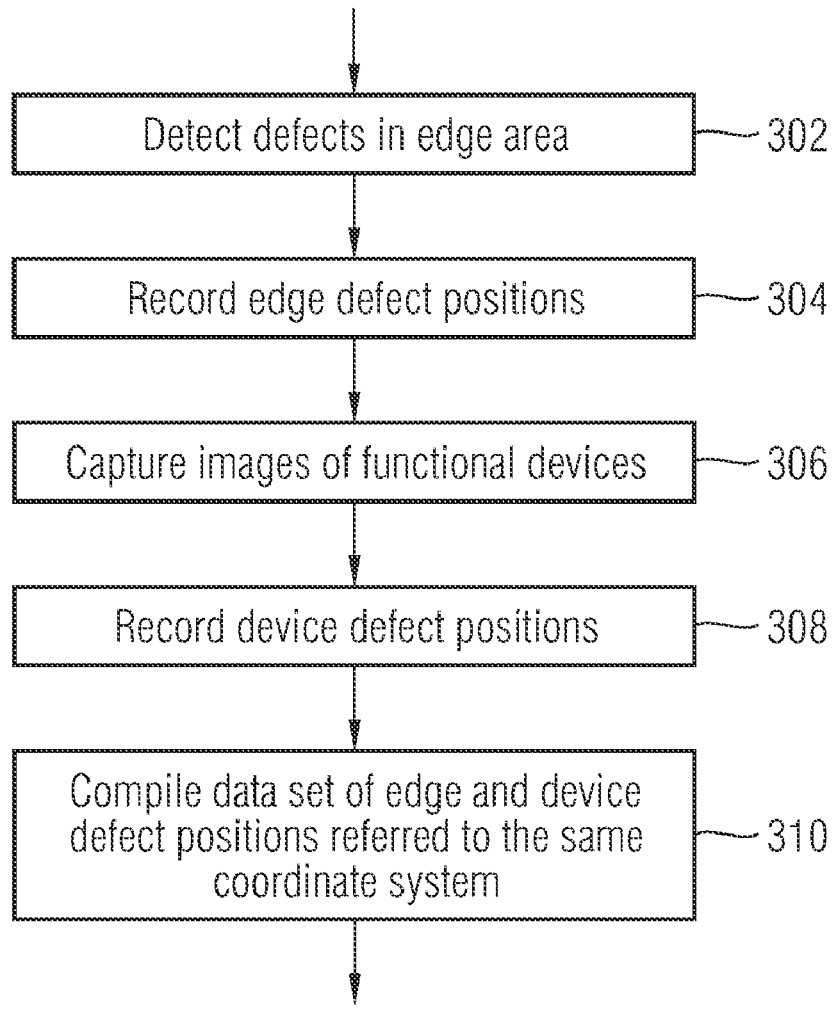
FIG. 3 is a simplified flowchart of a wafer inspection method according to a further embodiment.

FIG. 3 is a simplified flowchart of a wafer inspection method. Defects occurring in an annular edge area of the wafer are detected (302). The edge defect positions that are related to the detected defects are recorded (304), wherein further information about the defects may be related to the edge defect positions. In a functional area of the wafer that is surrounded by the edge area, images of functional devices are captured (306), wherein the functional devices may correspond, by way of example, to chip areas or sections of chip areas. The identified defect positions that are related to the functional devices are recorded (308), wherein further information about the device defects may be related to the device defect positions. A data set is compiled that includes the edge and device defect positions (310), wherein the edge and device defect positions are related to the same coordinate system. The coordinate system may be a device oriented coordinate system identifying the respective functional device and a position relative to the respective functional device.

In one embodiment, the edge defect positions are transformed into a Cartesian coordinate system. Further the edge defect positions may be mapped to virtual devices, wherein each virtual device is assigned to a sub-region of the edge area that is aligned to a grid which is obtained by extending into the edge region the grid to which the functional devices are aligned in the functional area.

The edge area may be inspected during alignment of the wafer to the optical inspection device. The defects in the functional area may be detected by comparing the captured images against each other or against reference images. The edge area of a successor wafer may be inspected during the optical inspection of an antecessor wafer of the same wafer lot to minimize overall inspection time.

Further, in course of the edge error detection, lithographic alignment marks may be evaluated for supporting the alignment of edge defect positions to the device coordinate system.

Figure 4:
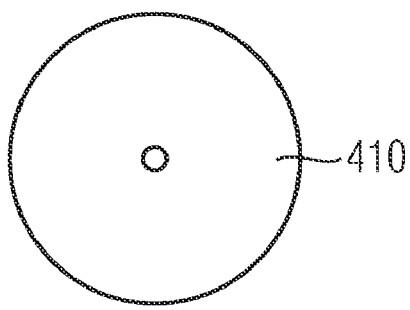
FIG. 4 is a schematic illustration of a computer program product according to yet another embodiment.

FIG. 4 refers to a computer program product that includes a computer storage medium 410, for example a disk, a magnetic hard drive or a flash memory medium. A computer code mechanism that is embedded in the computer storage medium may include a compiler code device that is configured to compile, from edge defect positions of edge defects occurring in an edge area of a wafer and from device defect positions that are related to defects occurring in a functional area of the wafer, a data set that includes the edge and the device defect positions related to the same coordinate system.

A computer mechanism may operate, for example, on a processor unit of an wafer inspection tool as described with reference to FIG. 1 or on a desk top computer, on a server or a work station. An edge defect data set including the edge defect positions of edge defects may be delivered from an edge inspection tool that may be integrated in a wafer inspection system as described with reference to FIG. 1 or from a stand-alone edge inspection tool. The data set including the device defects occurring in a functional area of the wafer may be delivered from a stand-alone optical image system or an optical image system that is integrated for example in a combined wafer inspection tool as described with reference to FIG. 1.

The compiler code device may be further configured to assign the edge defect positions to virtual devices, wherein each virtual device is assigned to a sub-region of the edge area. Each sub-region may be aligned to a grid which is obtained by extending the grid to which the functional devices are aligned in the functional area of the wafer into the edge region.

According to one embodiment, a wafer inspection system includes an edge defect detection mechanism for detecting defects occurring in an edge area of the wafer and for recording edge defect positions. The edge defect detection mechanism may include, by way of example, bright field cameras, dark field cameras or electron beam systems. The wafer inspection system includes further an optical inspection mechanism for capturing images of functional devices in a functional area of the wafer that is surrounded by the edge area and for recording device defect positions related to the functional devices. The optical inspection mechanism may include dark field cameras, bright field cameras or electron beam systems. A processor of the wafer inspection system that is configured to output a data set relating the edge and device defect positions to the same coordinate system may include the central processing unit of a computer, a support processor or an ASIC that executes a computer code embedded in a computer program product.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An inspection system comprising:
   an edge defect detection unit configured to detect defects occurring in an edge area of a wafer and to record edge defect positions into a coordinate system;
   an optical inspection unit configured to capture images of functional devices in a functional area of the wafer that is surrounded by the edge area and to record device defect positions related to the functional devices into the coordinate system; and
   a processor unit configured to output a data set relating the edge and device defect positions to the same coordinate system.

2. The inspection system of claim 1, comprising wherein the data set is configured to relate the device defect positions to the device coordinate system identifying a respective functional device and a position referenced to the respective functional device.

3. The inspection system of claim 2, comprising wherein the processor unit is configured to transform the edge defect positions into the device coordinate system.

4. The inspection system of claim 2, comprising wherein the processor unit is further configured to map the edge defect positions to virtual devices, each virtual device being assigned to a sub-region of the edge area that is aligned to a grid to which the functional devices are aligned along both planar dimensions.

5. The inspection system of claim 1, further comprising:
   a rotable support unit configured to align the wafer to the optical inspection device; and
   wherein the edge defect detection unit is further configured to inspect the edge area during the alignment.

6. The inspection system of claim 1, comprising wherein the optical inspection unit is further configured to detect defects via comparing the captured images against each other or against reference images.

7. The inspection system of claim 1, comprising wherein the edge defect detection unit is further configured to inspect the edge area of a successor wafer during the optical inspection of an antecessor wafer.

8. The inspection system of claim 1, comprising wherein the edge area overlaps the functional area.

9. A wafer inspection method comprising:
   detecting defects occurring in an edge area of the wafer;
   recording edge defect positions related to the detected defects into a coordinate system;
   capturing images of functional devices in a functional area of the wafer that is surrounded by the edge area;
   recording device defect positions related to the functional devices into a coordinate system; and
   compiling a data set including the edge and device defect positions, wherein the edge and device defect positions are related to the same coordinate system.

10. The inspection method of claim 9, wherein the device defect positions are related to the device coordinate system identifying a respective functional device and a position referenced to the respective functional device.

11. The inspection method of claim 10, comprising transforming the edge defect positions into the device coordinate system.

12. The inspection method of claim 11, comprising assigning the edge defect positions to virtual devices, wherein each virtual device is assigned to a sub-region of the edge area that is aligned to a grid to which the functional devices in the functional area are aligned along both planar dimensions.

13. The inspection method of claim 9, comprising inspecting the edge area during alignment of the wafer to the optical inspection device.

14. The inspection method of claim 9, comprising detecting defects in the functional area by comparing the captured images against each other or against reference images.

15. The inspection method of claim 9, wherein the edge area of a successor wafer is inspected during the optical inspection of an antecessor wafer.

16. The inspection method of claim 9, comprising wherein the edge area overlaps the functional area.

17. The inspection method of claim 10, comprising evaluating in course of the edge error detection, lithographic alignment marks for aligning the edge defect positions to the device coordinate system.

18. A computer program product comprising:
    a computer storage medium; and
    a computer code mechanism embedded in the computer storage medium and comprising:
    a compiler code device configured to compile, from edge defects positions of edge defects occurring in an edge area of a wafer and from device defect positions related to defects occurring in a functional area of the wafer, a data set that includes the edge and device defect positions referenced to a coordinate system.

19. The computer program product of claim 18, comprising wherein the compiler code device is configured to relate the device defect positions to the device coordinate system that identifies the respective functional device and a position referenced to the respective functional device.

20. The computer program product of claim 19, comprising wherein the compiler code device is further configured to assign the edge defect positions to virtual devices, each virtual device being assigned to a sub-region of the edge area, each sub-region being aligned to a grid to which the functional devices are aligned along both planar dimensions.

21. A wafer inspection system comprising:
    edge defect detection means for detecting defects occurring in an edge area of the wafer and for recording edge defect positions into a coordinate system;
    optical inspection means for capturing images of functional device in a functional area of the wafer that is surrounded by the edge area and for recording device defect positions related to the functional devices into a coordinate system; and
    a processor configured to output a data set relating the edge and device defect positions to the same coordinate system.

22. The wafer inspecting system of claim 21, comprising wherein the data set is configured to relate the device defect positions to the device coordinate system identifying a respective functional device and a position referenced to the respective functional device.

* * * * *